United States Patent [19]

Thompson

[11] Patent Number: 4,689,040
[45] Date of Patent: Aug. 25, 1987

[54] TIP FOR A PHACOEMULSIFICATION NEEDLE

[76] Inventor: Robert J. Thompson, 9900 Genesee Ave., San Diego, Calif. 92037

[21] Appl. No.: 728,493

[22] Filed: Apr. 29, 1985

[51] Int. Cl.$^4$ ............................................. A61B 17/20
[52] U.S. Cl. ..................................... 604/22; 604/268; 604/272; 128/305
[58] Field of Search ................ 128/305, 304, 751–758; 604/22, 21, 44, 117, 119, 164, 264, 268, 272, 274, 902, 411–413

[56] References Cited

U.S. PATENT DOCUMENTS

| | | | |
|---|---|---|---|
| 1,601,709 | 10/1926 | Anderson | 604/164 |
| 3,048,173 | 8/1962 | Kompelien et al. | 604/411 |
| 3,460,255 | 8/1969 | Hutson | 604/268 |
| 3,528,425 | 9/1970 | Banko | 128/305 |
| 3,589,363 | 6/1971 | Banko et al. | 128/276 |
| 3,732,858 | 5/1973 | Banko | 128/2 B |
| 3,805,787 | 4/1974 | Banko | 128/276 |
| 3,844,272 | 10/1974 | Banko | 128/2 B |
| 3,857,387 | 12/1974 | Shock | 128/24 A |
| 3,902,495 | 9/1975 | Weiss et al. | 128/276 |
| 4,132,227 | 1/1979 | Ibe | 604/27 |
| 4,320,761 | 3/1982 | Haddad | 128/305 |
| 4,515,583 | 5/1985 | Sorich | 604/22 |

OTHER PUBLICATIONS

"Phacoemulsification in the Posterior Chamber with Beveled Tip Down" by Martin, Cataract Magazine, Jan. 1985.

Advertisement by OcuCare in "Ophthalmic Surgery" Magazine, Nov. 1984, pp. 934–935.

Primary Examiner—Dalton L. Truluck
Assistant Examiner—Mario Costantino
Attorney, Agent, or Firm—Brown, Martin Haller & Meador

[57] ABSTRACT

An improved tip for a phacoemulsification needle having a lumen and a wall; wherein the improved tip comprises an oblique, generally concave face in side view and concentrates the majority of the effective cross-sectional area of the lumen toward the rear. An exemplary embodiment employs a maximum total face angle of 40 degrees with the face further comprising in side view from top to bottom: a first lead-in angle; a second horizontal section at a height of approximately 20-25 percent the needle diameter; and a third section defined as an arc of a circle extending tangential to the second horizontal section and extending to the top wall of the needle wherein the radius of the circle is approximately the distance between the second section and the upper wall. The improved tip is for use on hollow, ultrasonically vibrated needles of the type used for the surgical removal of cataract, abscess, hemorrhage, or other unwanted material. The improved tip is particularly designed to allow for the emulsification and aspiration of the lens of an eye in the lens chamber by increasing operative visability and reducing the incidence of pressure transients and surge, thereby reducing the danger of rupturing the posterior capsule and loss of vitreous. With the improved tip which permits material sculpting and manipulation, phacoemulsification can be accomplished without aid of another instrument.

7 Claims, 16 Drawing Figures

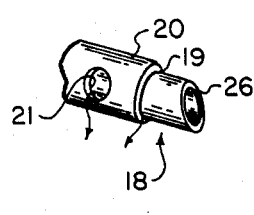
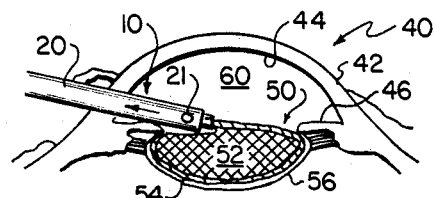
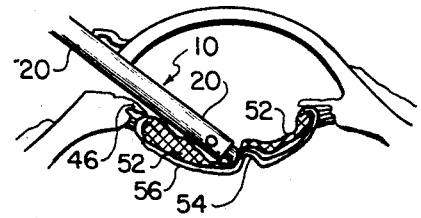
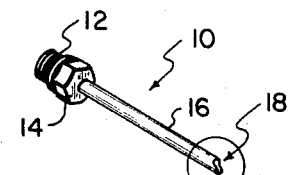
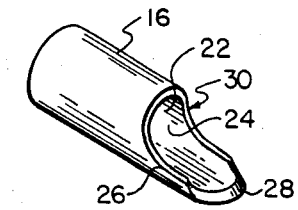
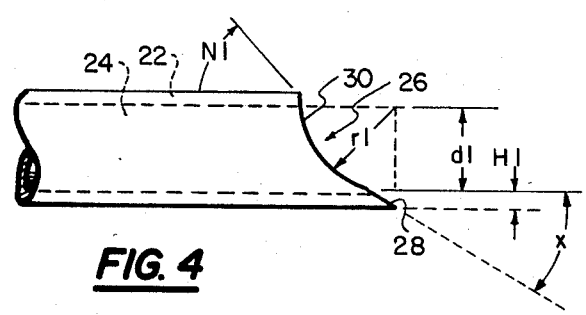
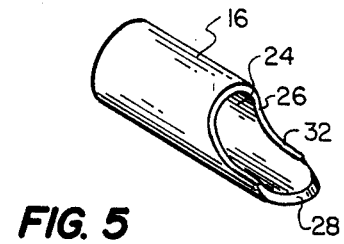
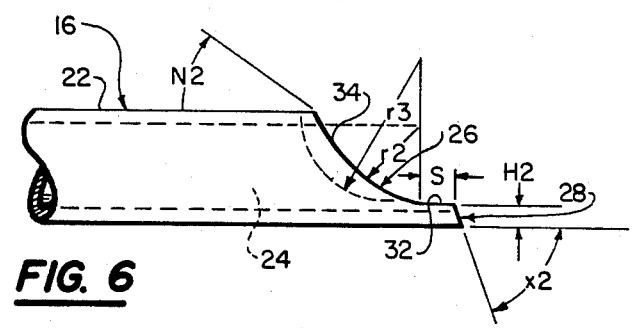

TIP FOR A PHACOEMULSIFICATION NEEDLE

BACKGROUND OF THE INVENTION

This invention relates in general to an improved tip for a hollow, ultrasonically vibrated needle and more particularly to an improved tip for a phacoemulsification needle such as used in the surgical device shown by U.S. Pat. No. 3,589,363 issued June 29, 1971 to A. Banko and C. D. Kelman for a Material Removal Apparatus and Method Employing High Frequency Vibrations. The aforesaid patent describes an instrument for breaking apart and removing unwanted tissue and material, especially a cataract located in the anterior chamber of the eye, by ultrasonically fragmenting the cataract while simultaneously introducing fluid into the eye chamber and withdrawing the fluid and fragmented cataract particles. Briefly the device described includes a hand piece having an operative needle vibrating in ultrasonic range. The needle shaft is hollow and is in turn surrounded by a tubular sleeve. In operation the needle shaft including the surrounding tubular sleeve are inserted into the anterior chamber of the eye. Irrigation fluid is introduced through the hollow sleeve to provide a replacement for fluid withdrawn or lost from the eye chamber. The removal of fluid and suspended material from the anterior chamber is called aspiration and ideally there is no change in fluid content or anterior chamber pressure as a result of irrigation-aspiration.

It is highly desirable to emulsify the lens nucleus in situ because removing the nucleus from its original position and emulsifying it elsewhere in the eye creates a high probability of damage to other eye tissue, such as to the iris and corneal endothelium. However, commonly, the lens is not emulsified in situ because of the problems hereinbelow described, particularly the great danger of rupturing the posterior capsule.

Basically the eye is separated into two chambers, an anterior and posterior. These elastic, pressure-responsive chambers are separated by a thin, cellophane-like diaphragm called the posterior capsule located behind the lens. If the posterior capsule encounters a sharp instrument, particularly a vibrating needle, it is easily punctured and, once its structural integrity is broken, the posterior capsule generally splits and tears. The result is quite catastrophic. Vitrious humor is lost and lens particles and other material fall into the posterior chamber resulting in many complications, dangers, and difficulties.

The relative fluid pressures in the anterior and posterior chamber greatly influence the probability of posterior capsule rupture. Ideally the pressure in the anterior chamber should be slightly greater than the pressure in the posterior chamber. This keeps the posterior capsule bowed posterially and rigid. If the pressure in the anterior chamber becomes equal to or less than the pressure in the posterior chamber, the capsule provides a very infirm work surface and presents itself for damage. Control of both the macro pressure differential, i.e. the general overall pressures within the chambers, and the micro pressure differentials, i.e. the transient localized pressure differential particularly near the needle tip, are important. The problem of control of fluid content and pressure within the anterior chamber of the eye during irrigation-aspiration is discussed in U.S. Pat. No. 3,902,495 to S. N. Weiss and A. Broadwin for a Flow Control System. Various changes have been introduced into the conventional apparatus external to the eye to control pressure which have made contributions toward controlling the micro pressures. However, some problems cannot be controlled in this means or have not been fully controlled.

Pressure in the anterior chamber may be equal to or less than the pressure in the posterior chamber due to leakage exterior to the posterior capsule. Also local pressure transients occur at the needle tip, particularly because of a condition called "surge". As will be more fully explained later, surge is caused when the needle tip is temporarily occluded by lens material. A high vacuum quickly builds up in the needle lumen partially because of inertial flow and the occlusion is cleared. However, the high vacuum existing in the aspirating system and needle is then quickly transferred to the area immediately adjacent the needle tip and exerts a strong drawing power on adjacent tissues. If the posterior capsule is nearby, particularly if is floppy or bulging due to incorrect macro pressure differentials, it may easily contact the tip or another tool and be damaged.

It is of course desirable to make as few incisions and as small of incisions in the eye as possible while performing phacoemulsification. However, it is often necessary to physically manipulate the lens or other material. Present needle tips have a flat, angled face which is generally unsuited for these purposes. Therefore, another instrument such as an elongated spatula is used. Insertion of a manipulating spatula requires either a larger incision so that the manipulating tool can be inserted alongside of the needle; or withdrawal of the needle, insertion, use and extraction of the spatula and reinsertion of the needle; or another incision and use of the spatula in conjunction with the needle. A problem with the later technique, other than the extra incision, is the great difficulty in simultaneously coordinating two hand-held instruments while looking through a microscope.

Therefore, it is desirable to have an instrument capable of emulsifying the lens of an eye, which greatly reduces the probability of posterior capsule rupture, especially where the lens is kept in its original position.

It is also desirable to eliminate or greatly reduce surge and its concomitant hazards.

It is particularly desirable that such instruments and results be achieved by modification of that portion of the phacoemulsification apparatus inserted within the eye.

It is also desirable to have a phacoemulsification needle better capable of material manipulation.

It is also desirable to have an improved phacoemulsification needle tip better suited for sculpting.

It is even further desirable to have an improved phacoemulsification needle capable of lens emulsification and removal without the aid of another instrument.

SUMMARY OF THE INVENTION

This invention is an improved tip for a phacoemulsification needle and it generally comprises an oblique, generally concave face in side view and concentrates the majority of the projected cross-sectional area of the lumen toward the rear of the tip. In an exemplary embodiment, the improved tip comprises an oblique generally concave face in side view with a maximum total face angle of 40 degrees; said face further comprises in side view from top to bottom: a first lead-in angle section; a second, horizontal section at height of approximately 20–25% the needle diameter; and a third section defined as the arc of a circle extending tangential to the second section and extending to the top wall of the needle; the radius of the circle being approximately the distance between the second section and the upper wall.

The improved needle tip of the present invention reduces surge and its associated dangers. Additionally, the improved needle tip of the present invention allows emulsification of the lens without need for an additional manipulation tool.

In the improved tip, the suction gradient and the fluid flow gradient is many times larger near the upper rear of the tip than near the fore point, where the gradients are very low. This stand-off feature tends to keep the aspirating needle from grabbing material such as the posterior capsule. The irregular face of the improved needle is not so easily occluded and the very high flow gradient at the top rear of the needle causes material chunks capable of occluding the needle to tumble and tear, thereby preventing occlusion.

The scoop-like fore section of the needle tip of the preferred embodiment may be used for sculpting material, for severing material from other material, and for probing to check depth of material. The scoop may also hold and move material to positions where it is safer to aspirate or emulsify and aspirate. Material may also be moved and manipulated by pushing the tip against it or by embedding the scoop-like end in the material so that some torsion may also be applied to the material.

These features of the improved tip allow for phacoemulsification of a lens in its original position without excessive danger of posterior capsule rupture. They also allow the lens to be fragmented and aspirated without the aid of an additional manipulation tool.

Other features and many attendant advantages of the invention will become more apparent upon a reading of the following detailed description together with the drawings wherein like reference numbers refer to like parts throughout. The drawings disclose by way of example, not by way of limitation, the principles of the invention and the structural implementation of the inventive concept.

BRIEF DESCRIPTION OF THE DRAWING

FIG. 1a is a perspective view of common prior art phacoemulsification tip.

FIG. 1b is a cross-sectional view of a prior art phacoemulsification needle in use in an eye.

FIG. 1c is a cross-sectional view of a prior art phacoemulsification needle in use.

FIG. 2 is a perspective view of a typical phacoemulsification needle having the improved tip of the present invention.

FIG. 3 is a perspective view of an exemplary embodiment of the phacoemulsification needle tip of the present invention.

FIG. 4 is a cross-sectional view of the exemplary embodiment of the phacoemulsification needle tip of FIG. 3.

FIG. 5 is an enlarged perspective view of a preferred embodiment of the phacoemulsification needle tip of the present invention as shown in FIG. 2.

FIG. 6 is a cross-sectional view of the needle tip shown in FIG. 5 as applied to a needle with a circular lumen.

FIG. 11b is a side view of FIG. 11a.

FIG. 12b is a side view of FIG. 12a.

DETAILED DESCRIPTION OF THE DRAWING

Figure 7:
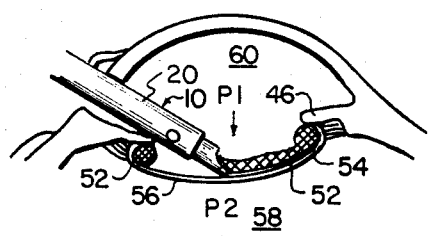
FIG. 7 is a cross-sectional view of a preferred embodiment of the phacoemulsification needle tip of the present invention in use when the anterior chamber pressure is greater than the posterior chamber pressure.

The environment of this invention is an ultrasonic phacoemulsification system. U.S. Pat. No. 3,589,363 described hereinbefore and which is incorporated herein by reference describes apparatus and method for the removal of material by employing high frequency vibration. Briefly, the aforesaid patent describes instruments and method for breaking apart and removing unwanted material, such as for surgically removing a cataract from the eye. The apparatus includes a hand piece having a needle with an operative tip vibrating at a frequency in the ultrasonic range. The term "ultrasonic" is used herein in a broad sense and encompasses frequencies in the range from 1,000–100,000 cycles per second. Typical ultrasonic frequencies which are utilized are in the range between 15,000 and 50,000 cycles per second with 40,000 cycles per second preferred for the present invention. The amplitude is controllable over a range with 1 mm typically being utilized. The operative needle has a hollow, elongated portion or shaft comprised of a thin wall enclosing a lumen. The shaft is, in turn, surrounded by a tubular irrigation sleeve forming an annular passage. Irrigation fluid is introduced into an eye chamber through the annular passage between the irrigation sleeve and the needle. Fluid and fragmented material are aspirated from the eye through the needle lumen.

Although for purposes of this description, the environment is described in terms of having a tubular irrigation sleeve encompassing the needle, this common metod of irrigation is used for illustrative purposes only and other methods of irrigation, such as by a separate irrigation source, may be employed with the present invention.

Although the present invention has been described in use primarily with regard to the break-up and removal of eye lens material, the term "phacoemulsification" is a general term for ultrasonic systems of the type described, and it is understood that such systems including the present invention are applicable to many other uses.

With reference now to the drawings, and more particularly to FIG. 2 thereof, there is shown a typical phacoemulsification needle, shown generally as 10. The needle 10 generally comprises a threaded rear portion 12, a nut portion 14, an elongated, thin walled shaft portion 16 having a lumen 24, and tip portion 18. As described above, the needle is attached to a hand piece (not shown) for vibrating the needle in the ultrasonic range. Typically, apparatus is attached to the hand piece for controllably supplying a vacuum to the needle lumen and for controllably furnishing irrigation fluid to an irrigation sleeve 20, as shown in FIG. 1a, surrounding the needle 10. A needle 10 with an outside diameter of 0.030 to 0.050 inches is desirable. On a common needle in use, the outside diameter of the shaft 16 is 0.043 inches and the thickness of the shaft wall 22 is approximately 0.0035 inches. In cross-section, the shaft 16 may be circular as shown in FIG. 3 or slightly elliptical as shown in FIG. 5.

Shown in FIG. 1a is a typical prior art needle tip 18 and irrigation sleeve 20. The needle shaft 16 terminates in a flat cut end face 26. Irrigation fluid passing through the sleeve 20 exits at the end annulus 19 or alternatively via irrigation ports 21 on either side of the sleeve 20.

An exemplary embodiment of the improved tip for a phacoemulsification needle is shown in perspective view in FIG. 3 and in cross-sectional view in FIG. 4. Needle shaft 16, having a generally circular wall 22 enclosing lumen 24, terminates in a cut face 26. As seen in FIG. 4, the needle tip commences at the bottom fore with a first lead-in bevel section 28 of height H1. A second face section 30 leading from the top of the first lead-in bevel section 28 to the top rear of the tip, is generally concave. In the exemplary embodiment, the concave face portion 30 is defined as the arc of a circle of radius r1 of approximately 1.5 times the shaft diameter. The overall face angle N1 between the bottom fore point of the tip and the top rear point on the tip is less than 50 degrees.

With reference now to FIGS. 5 and 6, there is shown a preferred embodiment of the improved needle tip of the present invention. FIG. 5 is an enlarged perspective view of the tip shown in FIG. 2. The tip shown in FIG. 5 is cut on a slightly elliptical shaft, although a circular shaft is also suitable. As shown in cross-section FIG. 6 the preferred tip face 26 configuration comprises a first lead-in bevel section 28, a second, horizontal, face section 32, and a third face section 34. The overall face angle N2 of the preferred embodiment is less than 45 degrees, preferably about 30-40 degrees. The height H2 of the first lead-in bevel 28 is commonly in the range of 20-25 percent of the shaft diameter and a height H2 of approximately 0.010 inches has been found satisfactory for most purposes. In the preferred embodiment, the angle X2 of the first lead-in bevel section 28 is 45 degrees or less. In alternate embodiments, if the height H2 is small, then the lead-in bevel angle X2 is not as critical and may be greater than 45 degrees. The length S of the second, horizontal face section 32 is preferably in the range of 0.010-0.020 inches. The third face section 34 extending from the second face section 32 to the top wall 22 of the needle is preferably concave in side view and is preferably designed as the arc of a circle of radius of r2 to radius r3 where r2 is the height of the lumen 24 minus the height H2 of the first lead-in bevel, and r3 is approximately 1.5 times r2. The arc is tangential to horizontal, second face section 32 in the preferred embodiment of the invention as shown in FIG. 6. With radius r2 as above defined, over half of the exposed cross-sectional area of the lumen is located in the rear 0.008 inches of the tip, while less than half of the lumen cross-sectional area is exposed in the fore 0.0485 inches of the tip. This fore section of the tip will be referred to generally as the "stand-off" section. As seen in FIG. 5 the stand-off section of the needle tip has a shape that is shovel, spoon, or scoop-like.

During aspiration, a vacuum is applied to the needle lumen 24 and fluid and other material flows into the orifice of the tip 18 and through the lumen 24. Thus there is a suction gradient and a fluid flow gradient in and around the needle tip. With the improved tip of the present invention, particularly the tip configuration shown in FIG. 5, this suction gradient and fluid flow gradient near the rear of face 26 of the needle tip is many times larger than that at the fore face of the lead-in bevel section 28.

The advantages of these needle tip features will become apparent with the following description of the environment of use.

The improved needle tip of the present invention is particularly suitable for the break-up and removal of lens nucleus without removing the nucleus from its natural position in the eye.

It may be desirable to remove the lens from an eye because of cataract or other damage to the lens. Shown in FIG. 1b is one phacoemulsification method of lens removal. FIG. 1b is a cross-sectional view of a human eye, shown generally as 40, and a phacoemulsification needle, shown generally as 10, in use. The eye 40 generally comprises a cornea 42 having an inner layer called the corneal endothelium 44, and iris 46. The lens, shown generally as 50, is comprised of a nucleus 52 and cortex 54. A thin lining, the posterior capsule 56, separates the lens chamber from the vitreous or posterior chamber 58.

The size and hardness of the lens nucleus 52 varies greatly, but in general with age the lens nucleus 52 grows, becomes harder and approaches the posterior capsule 56. As shown in FIG. 1b, after common preparatory steps, the phacoemulsification needle 10 is inserted into the eye through an insertion to encounter the lens 52. Irrigation sleeve 20 on the needle may provide irrigation fluid which exits into the interior chamber via the annular orifice 19 between the end of the sleeve 20 and the needle or through irrigation ports 21 located on each side near the end of the sleeve 20. Upon engaging the lenses nucleus 52 a burst of ultrasonic vibration is applied to the needle for cutting. Usually bursts of 0.5–2.0 seconds are used but sometimes longer bursts of 3–5 seconds may be used. In the vibratory mode the needle tip cuts and breaks away a chunk of lens material. This material then may be aspirated through the needle lumen 24 out of the eye. In this manner, the lens 52 is fragmented and removed from the eye.

Another important concept must be introduced at this point. Basically the eye is comprised of two chambers: the anterior chamber 60 which includes the lens 50 chamber and the posterior chamber or vitrious capsule 58. The primary seal between these two chambers is the posterior capsule 56 of the lens.

The phacoemulsification is essentially performed in a closed chamber, the anterior chamber 60 separated by a thin flexible diaphragm-like membrane, the posterior capsule 56, from another closed chamber, the posterior chamber 58. In dealing with the addition and subtraction of material from an enclosed chamber, it is extremely important that a proper balance be established between the irrigation and aspiration flows to insure stability within the chamber. Ideally the pressure P1 in the anterior 60 is slightly greater than the the pressure P2 in the posterior chamber 58. This will tend to hold the posterior capsule hot during phacoemulsification, a condition which as will be explained is highly desirable.

This condition of the posterior capsule is shown in FIG. 7.

Figure 8:
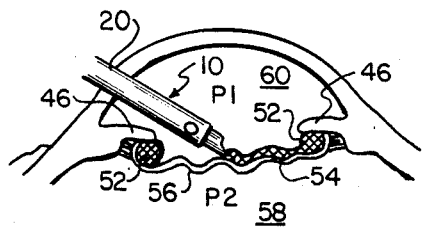
FIG. 8 is a cross-sectional view of a preferred embodiment of the phacoemulsification needle tip of the present invention in use when the anterior chamber pressure is approximately equal to the posterior chamber pressure.

FIG. 8 shows the condition of the posterior capsule 56 when P1 is approximately equal to P2. The capsule becomes very flexible and floppy and vacilates with each temperal pressure change.

Figure 9:
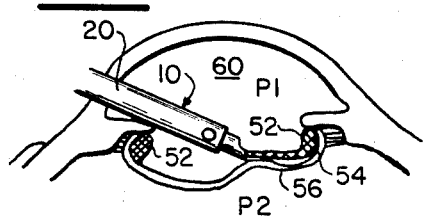
FIG. 9 is a cross-sectional view of a preferred embodiment of the phacoemulsification needle tip of the present invention in use when the anterior chamber pressure is less than the posterior chamber pressure.

FIG. 9 illustrates the condition of the posterior capsule 56 when P1 is less than P2. The posterior capsule 56 bows into the anterior chamber 60. In addition to these more prolonged pressure conditions, pressure transients are periodically being induced at the needle tip 18. During aspiration, near the needle tip 18 there is a localized lower pressure zone.

Various methods have been employed in the apparatus supplying the irrigation fluid and the aspiration vacuum to assure balance between these two flows.

Another common phenomenon creating a localized pressure transient is called "surge". U.S. Pat. No. 3,902,495 described hereinbefore and incorporated herein by reference, describes the problem of surge and a fluid control system to aid in its reduction. Surge occurs when the tip orifice is occluded by lens material. During such occlusion, fluid is prevented from entering the hollow tip and a strong vacuum is created in the needle lumen. If the tip opening is suddenly uncapped by breakup of the occlusion, the high vacuum existing in the needle and aspirating system is quickly transferred to immediately adjacent the needle tip with a resultant strong attraction for nearby material, which seems to "jump" at the tip.

The great danger of improper pressure differentials and surge is that they may cause the tip to contact and rupture the posterior capsule 56 which is disasterious. The diaphragm-like capsule 56 is quite strong as a membrane, however once its integrity is breached, it becomes fragile and easily splits, even if only a small hole is created. FIG. 1c illustrates a prior art, flat-faced needle 10 that has encountered the posterior capsule 56. This will almost inverably result in rupture.

The improved needle tip of the present invention is less susceptible to surge and is less likely to rupture the posterior capsule. The relatively shallow face angle N of the tip of the present invention assures that the surgeon observing from above can see the entire tip face 26 including the first lead-in bevel section 28. This allows the surgeon to be more accurately aware of approaching the posterior capsule 56 and be to more visually aware of potential occlusions. The elongated irregular face 26 is not as easily blocked. The extremely high aspiration flow gradient near the top rear of the tip immediately causes a tearing and tumbling effect on material as it nears occlusion of the tip, thus preventing total occlusion. The stand-off section tends to hold material which should not be aspirated such as the posterior capsule 56, away from the high vacuum portion of the tip orifice.

The above-referenced tip features and advantages are shown in FIGS. 7, 8, and 9. FIG. 7 illustrates the condition wherein P1 is greater than P2 so that as the lens nucleus 52 is removed, the lens cortex 54 and posterior capsule 56 remain taut and in position. The shallow total face angle N allows the surgeon to observe the fore end of the tip so that it avoids the posterior capsule 56 and the tip configuration tends to prevent surges as described above.

FIG. 8 illustrates the condition where P1 is approximately equal to P2. This may be caused by an imbalance in the input and output fluids or by a leakage external to the posterior capsule 56. With P1 approximately equal to P2 as the hard lens nucleus 52 is mulsified and aspirated the residual cortex 54 and the posterior capsule 56 become very flexible and floppy. This is a dangerous condition because these materials may easily and rapidly occlude the needle and even rupture, given the opportunity. As shown in FIG. 8, the hold-off portion of the needle creates some firmness under the working area. Also, the very low aspiration fluid flow gradient near the tip does not strongly attract the flaccid materials.

FIG. 9 illustrates the condition where P1 is less than P2. This is typically caused by imbalance in fluid flow or leakage. With P1 less than P2, as the rigid lens nucleus is emulsified and aspirated, the posterior capsule 56 bulges up into the interior chamber 60. With this condition, it is difficult to remove the remaining lens nucleus 52, because the bulging posterior capsule 56 will retreat under physical force yet be highly attracted to the aspirational forces. The needle tip of the present invention tends to stabilize the situation, the stand-off section adds some rigidity to the posterior capsule 56 to help control the bulge. It also holds this material away from the high fluid flow and suction gradient area near the rear of the needle tip.

The scoop-like fore section of the improved tip of the present invention acts as a mechanical severing device which can cut, scoop, or sculpt material. The scoop is suited for physically moving material, to separate material from other material, or to move material to a position where it may be less dangerously emulsified or aspirated. The scoop is better suited to cutting sideways than is a conventional needle tip. The scoop end may also be used to probe and check material depth.

Figure 10:
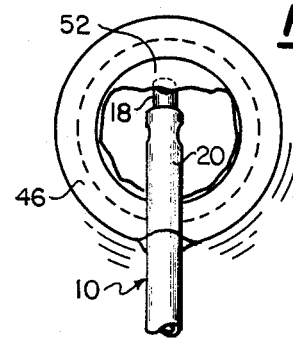
FIG. 10 is a top view of the needle tip used in FIG. 7 to remove the lens center.
Figure 11A:
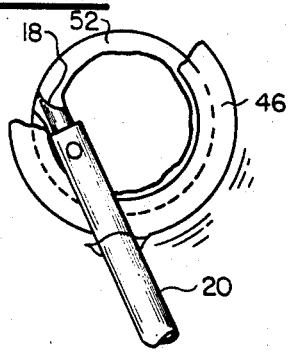
FIG. 11a is a top view showing use of the tip to sever the remaining lens donut.
Figure 11B:
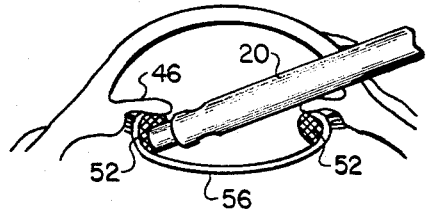
Figure 12A:
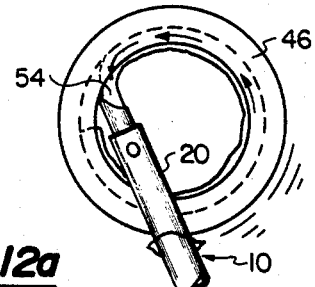
FIG. 12a is a top view showing use of the needle tip to separate the lens donut from the posterior capsule for emulsification.
Figure 12B:
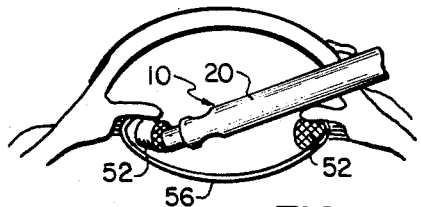

FIGS. 10, 11 and 12 illustrate a technique utilizing the improved needle tip of the present invention allowing emulsification and aspiration of the lens nucleus in its original location without the aid of another instrument. As shown in FIG. 7 in cross-view, the center of the nucleus 52 is removed until only a donut of nucleus remains under the iris 46. This is shown in top view in FIG. 10. FIG. 11a is a partially cut away top view of the lens donut 52 remaining. The needle tip 18 engages the lens donut 52 toward one side and severs it. This is shown in cross-section in FIG. 11b. Once the lens donut 52 is severed or nearly so, the donut may be collapsed and moved away from the vicinity of the posterior capsule 56 for quicker and safer emulsification and removal. This is shown in top view in FIG. 12a and in side view in FIG. 12b. Once the donut is severed and the engaged end is brought out from under the iris 46 and entirely into the viewing area, it is possible to continuously engage it and emulsify it in one location. As shown by the arrows in FIG. 12a the lens donut 52 will rotate and feed into the needle tip 18.

It can been seen that the needle tip of the present invention provides an improved tip for operation involving phacoemulsification-like techniques.

Although particular embodiments of the invention have been illustrated and described, modifications in changes will become apparent to those skilled and the art and it is intended to cover in the appended claims such modifications and changes as come within the true spirit and scope of the invention.

Having described my invention, I now claim:

1. In a phacoemulsification needle having a proximal end attachable to a phacoemulsification device and a distal end insertable into an eye; the needle having a central longitudinal axis extending from the proximal end to the distal end; a bore within the needle concentric to the central axis thereof, so as to form a lumen, the lumen having side walls therearound, having inner and other surfaces with an opening at the proximal and distal ends of the needle, an improved tip comprising:
- a tip formed by the distal opening which when viewed from an angle perpendicular to said central axis has a side view comprising:
  - a top wall located at a needle side wall on one side of said central axis;
  - a bottom wall located at a needle side wall on the opposite side of said central axis, and a tip face extending between said top and bottom walls;
  - said bottom wall of the tip forms a distally projecting tip section which when viewed from an angle perpendicular to said longitudinal axis and parallel to said bottom wall has a leading edge between said outer and inner sidewall surfaces formed at an angle of between 15 and 60 degrees to said longitudinal axis; and
  - said tip face has a concave outline extending from the inner surface of said bottom wall to the inner surface of said top wall which has a radius of approximately 1 to 1½ times the diameter of said lumen.

2. In a phacoemulsification needle having a proximal end attachable to a phacoemulsification device and a distal end insertable into an eye; the needle having a central longitudinal axis extending from the proximal end to the distal end; a bore within the needle concentric to the central axis thereof, so as to form a lumen, the lumen having side walls therearound, having inner and other surfaces with an opening at the proximal and distal ends of the needle, an improved tip comprising:
- a tip formed by the distal opening which when viewed from an angle perpendicular to said central axis has a side view comprising:
  - a top wall located at a needle side wall on one side of said central axis;
  - a bottom wall located at a needle side wall on the opposite side of said central axis, and a tip face extending between said top and bottom walls;
  - said bottom wall of the tip forms a distally projecting tip section which when viewed from an angle perpendicular to said longitudinal axis and parallel to said bottom wall has a leading edge between said outer and inner sidewall surfaces formed at an angle of between 15 and 60 degrees to said longitudinal axis; and
  - tip side walls extending vertically from said bottom wall having a height greater than the thickness of said bottom wall but less than or equal to 40% of the separation between said bottom and top walls with said tip side walls having top edges extending substantially parallel to said central axis between said distally extending tip and said top wall, said top edges having a predetermined length greater than the thickness of said bottom wall.

3. The tip of claim 2 wherein said tip face has a concave outline extending between the top edges of said tip side walls and said top wall.

4. The tip of claim 3 wherein said outline is defined as an arc of a circle for which said top edge of said tip side walls is a tangent, having a radius equal to the distance between said tip side walls and said top side.

5. The tip of claim 2 wherein said tip face has a maximum total face angle of approximately 50 degrees.

6. The tip of claim 2 wherein said tip side walls have a height of between 20 to 25 percent of the diameter of said needle.

7. The tip of claim 6 wherein the majority of the projected cross-section of said lumen is at least 0.025 inches from a foremost extension of said distal end.

* * * * *